United States Patent [19]

Batchelder et al.

[11] Patent Number: 5,220,403
[45] Date of Patent: Jun. 15, 1993

[54] APPARATUS AND A METHOD FOR HIGH NUMERICAL APERTURE MICROSCOPIC EXAMINATION OF MATERIALS

[75] Inventors: John S. Batchelder, Somers; Philip C. D. Hobbs, Briarcliff Manor; Marc A. Taubenblatt, Pleasantville, all of N.Y.

[73] Assignee: International Business Machines Corporation, Armonk, N.Y.

[21] Appl. No.: 954,282

[22] Filed: Sep. 30, 1992

Related U.S. Application Data

[62] Division of Ser. No. 667,773, Mar. 11, 1991.

[51] Int. Cl.⁵ .................. G01B 9/02; G01N 21/65; G01N 21/35
[52] U.S. Cl. .................. 356/345; 250/358.1; 250/360.1; 356/301; 356/349; 356/360; 356/432
[58] Field of Search .......... 356/301, 345, 349, 360, 356/432; 250/358.1, 359.1, 360.1

[56] References Cited

U.S. PATENT DOCUMENTS

| | | |
|---|---|---|
| 3,013,467 | 12/1961 | Minsky . |
| 3,034,398 | 5/1962 | Barnes et al. . |
| 3,055,258 | 9/1962 | Hurvitz . |
| 4,204,771 | 5/1980 | Shull et al. ............... 356/346 |
| 4,297,032 | 10/1981 | Temple ..................... 356/366 |
| 4,353,618 | 10/1982 | Hagner et al. ............ 351/16 |
| 4,555,767 | 11/1985 | Case et al. ................ 364/563 |
| 4,615,620 | 10/1986 | Noguchi et al. .......... 356/378 |
| 4,625,114 | 11/1986 | Bosacchi et al. ......... 250/341 |
| 4,724,322 | 2/1988 | Knowles et al. .......... 250/341 |
| 5,004,307 | 4/1991 | Kino et al. . |
| 5,087,121 | 2/1992 | Kakuchi et al. ........... 356/73 |

OTHER PUBLICATIONS

R. L. Jungerman, P. C. D. Hobbs, and G. S. Kino, "Phase sensitive scanning optical microscope", App. Phys. Lett. 45 (8), pp. 846-848 (Oct. 15, 1984).

George A. Wardly, "Electrostatic Wafer Chuck for Electron Beam Microfabrication", Rev. Sci. Instrum., vol. 44, No. 10, pp. 1506-1509 (Oct. 10, 1973).

Philip C. D. Hobbs & Gordon S. Kino, "Generalizing the confocal microscope via heterodyne interferometry and digital filtering", Journal of Microscopy, vol. 160, Pt. 3, pp. 245-264 (Dec., 1990).

*Primary Examiner*—Vincent P. McGraw
*Attorney, Agent, or Firm*—Ratner & Prestia

[57] ABSTRACT

Apparatus and a method for performing high resolution optical imaging in the near infrared of internal features of semiconductor wafers uses an optical device made from a material having a high index of refraction and held in very close proximity to the wafer. The optical device may either be a prism or a plano-convex lens. The plano-convex lens may be held in contact with the wafer or separated from the wafer via an air bearing or an optical coupling fluid to allow the sample to be navigated beneath the lens. The lens may be used in a number of optical instruments such as a bright field microscope, a Schlieren microscope, a dark field microscope, a Linnik interferometer, a Raman spectroscope and an absorption spectroscope.

4 Claims, 13 Drawing Sheets

APPARATUS AND A METHOD FOR HIGH NUMERICAL APERTURE MICROSCOPIC EXAMINATION OF MATERIALS

This application is a division of application Ser. No. 07/667,773, filed Mar. 11, 1991.

BACKGROUND OF THE INVENTION

The present invention concerns apparatus and a method which uses microscopy to determine characteristics of materials having relatively high indices of refraction and in particular, to apparatus and a method for inspecting semiconductor wafers from the back side, using a lens which has a relatively high numerical aperture and which is either in contact with or very close to being in contact with the wafer.

As integrated circuits are designed to include more and more components, the individual components are designed to be smaller and smaller. Some components, however, such as storage capacitors for dynamic random access memory (DRAM) cells, cannot be made smaller than a defined minimum size without degrading their performance. Recently, the numbers of components of this type which may be placed on an integrated circuit has been increased through the use of three-dimensional structures such as trenches.

Currently these trenches have diameters of between one and two microns ($\mu$m), depths of six to eight $\mu$m and aspect ratios (depth to diameter) of eight to one. In the near future, devices having aspect ratios approaching 100 to 1 and diameters of less than one $\mu$m may become feasible. fabricated on an integrated circuit,- they make visual inspection of the capacitors almost impossible even with a powerful microscope. This is because silicon and gallium arsenide are extremely lossy at the optical frequencies which are high enough to resolve the trench structures. At present, the dominant method of inspecting components of this type is to saw the wafer so that the components may be viewed from the side using a scanning electron microscope. This technique is time consuming and it destroys the wafer. Consequently, it is difficult to determine the electrical properties of an observed structure.

Silicon and gallium arsenide are transparent to infrared radiation having wavelengths between 1.2 and 15 $\mu$m. Backside inspection using infrared microscopy is routinely performed for inspecting flip-chip bonding pads, making picosecond voltage measurements and various photothermal and photoacoustic measurements. Unfortunately, however, all currently available infrared microscopes are limited to numerical apertures between 0.5 and 0.8. This results in a lateral resolution of 1.5 to 2.5 $\mu$m which is inadequate to resolve sub-micron trenches.

U.S. Pat. No. 4,625,114 to Bosacchi et al. concerns a technique for determining the thickness of thin films through the use of frustrated total internal reflection. A hemicylindrical lens, in intimate contact with the top surface of a substrate (semiconductor wafer) upon which thin films (epitaxial layers) have been deposited, is used to couple infrared radiation into the thin film structure over a wide range of angles. The instrument determines the thickness of a layer by identifying a single angle at which frustrated total internal reflection occurs. This instrument does not form images and is insensitive to properties of the other side of substrate.

U.S. Pat. No. 4,555,767 to Case et al. relates to apparatus which measures the thickness of a uniform layer of epitaxial silicon using a Fourier transform IR spectrometer. Measured values of spectral reflectance are correlated with theoretical reflectance values to determine the actual thickness of the epitaxial layer.

U.S. Pat. No. 4,615,620 to Noguchi et al. concerns apparatus for measuring the depth of fine engraved patterns. Pits having widths of between 1 and 3 $\mu$m and pitches of between 2 and 3 $\mu$m may be measured using radiation which varies in wavelength from 300 nanometers (nm) to 800 nm. The apparatus is a non-contact system which irradiates the top surface of the substrate with light of varying wavelength. The measurement is based on the detection of the intensity of a diffraction ray from which the contribution of the 0th order wavelength has been excluded.

U.S. Pat. No. 3,034,398 relates to an in-line infrared spectrometer which uses lenses and prisms made from germanium or silicon.

SUMMARY OF THE INVENTION

The present invention is embodied in an optical metrology system which measures internal features of an object having a relatively high refractive index. The system uses imaging apparatus coupled to a surface of the object to measure internal features of the object. The imaging apparatus includes an optical device which has a refractive index that is approximately equal to the refractive index of the substrate. The system is configured to couple high angle rays in the object into rays which propagate through the imaging apparatus.

According to one aspect of the invention, the object is a semiconductor wafer and the optical device is a prism which is configured to couple high angle rays into the wafer to produce high angle rays which are reflected from topological features on the front of the wafer.

According to another aspect of the invention, the optical device is a plano-convex lens having a relatively high numerical aperture which is configured to couple high angle rays from the substrate into rays which propagate in air. The optical metrology system uses the plano-convex lens as the objective lens of an infrared microscope.

According to another aspect of the invention, the optical device is coupled to the back side of the substrate by an air bearing which holds the device in close proximity to the substrate.

According to yet another aspect of the invention, the optical device is coupled to the back side of the substrate using a substance having a relatively large refractive index, through which at least some of the light is transmitted via frustrated total internal reflection.

DETAILED DESCRIPTION

Overview

The present invention is an optical instrument which may be used for imaging and metrology of semiconductor wafers from the back side. A key component of the optical instrument is a lens or prism that is formed from a material having a refractive index that is close to that of the semiconductor material. This device is coupled to the semiconductor wafer in a manner that allows high angle rays, which would normally be reflected at the semiconductor-air interface, to be coupled out of the semiconductor wafer as propagating rays in space. Using one coupling method, the lens or prism is held in a fixed position on the wafer. Other coupling methods, however, allow the device to be moved across the back surface of the wafer.

A number of optical instruments may be formed using the lens. These include a bright field microscope, a confocal microscope, a Schlieren microscope, a dark field microscope, a Linnik interferometer, a Raman spectroscope and other instruments which are useful in wafer metrology.

While the discussion below concerns inspection of semiconductor wafers, it is equally applicable to the internal inspection of other materials having relatively high indices of refraction, such as glass and water.

DETAILED DESCRIPTION OF THE EXEMPLARY EMBODIMENTS OF THE INVENTION

The lateral resolution of a light microscope, $\Delta x$ is determined by its operating wavelength in vacuo, $\lambda_0$, and its numerical aperture, NA. The numerical aperture of a lens is given by equation (1).

$$NA = n \sin \Theta \tag{1}$$

where n is the refractive index of the lens material and $\Theta$ is the half angle of the incident light cone. In air or in a vacuum where n is equal to 1, the numerical aperture is constrained to be less than unit. The lateral resolution $\Delta x$ is given by equation (2).

$$\Delta x = \frac{\alpha \lambda_o}{NA} \tag{2}$$

Where $\alpha$, which depends on the system details and the exact definition chosen for resolution, is greater than 0.2 and usually less than 1.0. For optical wavelengths close to 1.3 $\mu$m, silicon and gallium arsenide have refractive indices of approximately 3.5 and 3.34, respectively. Thus, inside these materials, light having a wavelength of 1.3 $\mu$m in a vacuum has a wavelength of less than 400 nm, equivalent to near ultraviolet in air. Other semiconductor materials, such as indium phosphide, indium antimonide, gallium phosphide and germanium also have relatively high refractive indices in the near infrared.

If light can be coupled into high-angle rays in a lens made from one of these materials, it is possible to achieve a numerical aperture of three or more. As set forth in equation (2), this would produce an improvement in lateral resolution to 0.4 $\mu$m or better, which would greatly improve the ability to inspect trenches from the back side of the wafer.

Figure 2B:
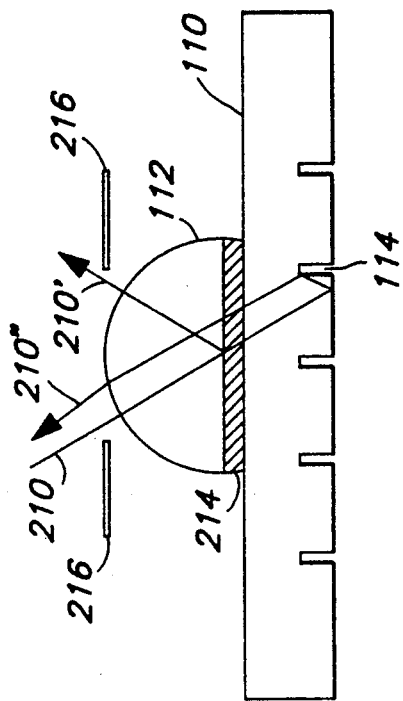
FIGS. 2a through 2d are elevation drawings which illustrate different configurations of the instrument shown in FIG. 1b.
Figure 2D:
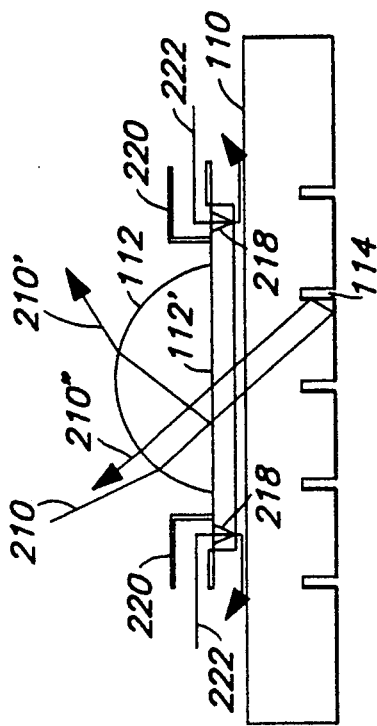
Figure 2A:
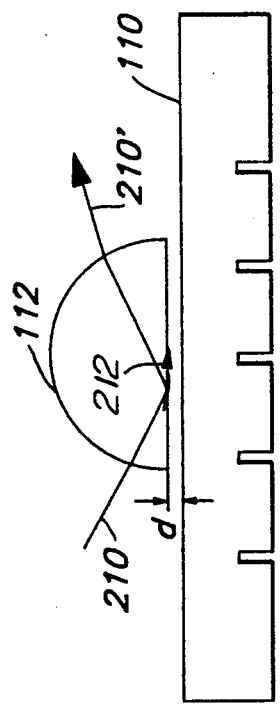

The difficulty in using this system involves the coupling of high-angle light rays from the silicon wafer into the lens. These waves are highly evanescent in air. For example, as illustrated in FIG. 2a, a ray 210 propagating through the lens at an angle of 66° from the normal to a silicon air interface, becomes an evanescent wave 212 which dies off as $e^{-kz}$ where k is given by equation (3)

$$k = \frac{2\pi}{\lambda_0} ((3.5 \sin(66°))^2 - 1)^{\frac{1}{2}} \tag{3}$$

From this equation, k is approximately equal to 14.5 $\mu m^{-1}$, so the energy density of the plane wave is reduced by a factor of approximately 5 trillion when a gap of 1 $\mu$m exists between the lens and the back surface of the wafer. In FIG. 2a, if the distance d is approximately 1 $\mu$m, substantially all of the wave energy is reflected from the silicon-air interface as a wave 210'.

Figure 2C:
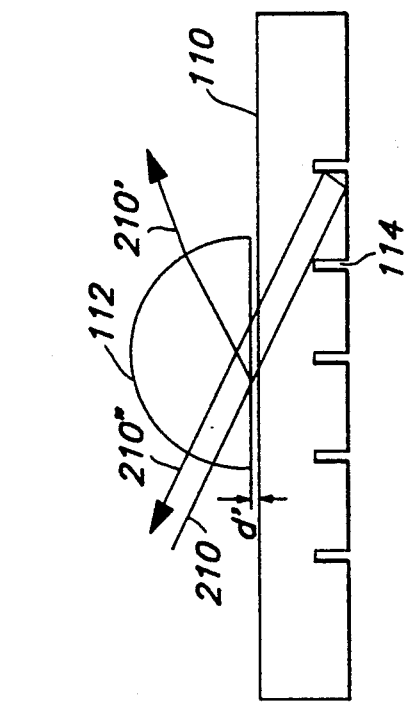

If, however, as illustrated in FIG. 2c, the air gap between the bottom of the lens and the back surface of the wafer is only a few tens of nanometers, much more of the evanescent wave propagates into the wafer from the lens. If a parallel polarized plane wave having an incident angle of $\Theta$ meets a thin planar air gap of thickness a (index of refraction, $n_2 = 1$) between two silicon surfaces ($n_1 = 3.5$), where $\Theta$ is beyond the critical angle, the reflection coefficient, r, due to frustrated total internal reflection is given by equation (4).

$$r = \frac{1 + \delta^2}{1 - \delta^2 + i2\delta \coth(ka)} \tag{4}$$

where i is the complex value $(-1)^{\frac{1}{2}}$, $\delta$ is given by equation (5), a is the thickness of the gap between the two silicon surfaces, and k is given by equation (6).

$$\delta = (\sin^2(\theta) - (n_2/n_1))^{\frac{1}{2}} \tag{5}$$

$$k = \frac{2\pi}{\lambda_o} (n_1^2 \sin \theta - n_2^2)^{\frac{1}{2}} \tag{6}$$

For an incident angle of 66° and an air gap of 50 nm, this corresponds to a reflection coefficient of 6% or a transmission of 94% of the plane wave energy through the air gap. The inventors have determined that excellent coupling occurs when an air gap of up to 50 nm can be maintained.

Figure 1A:
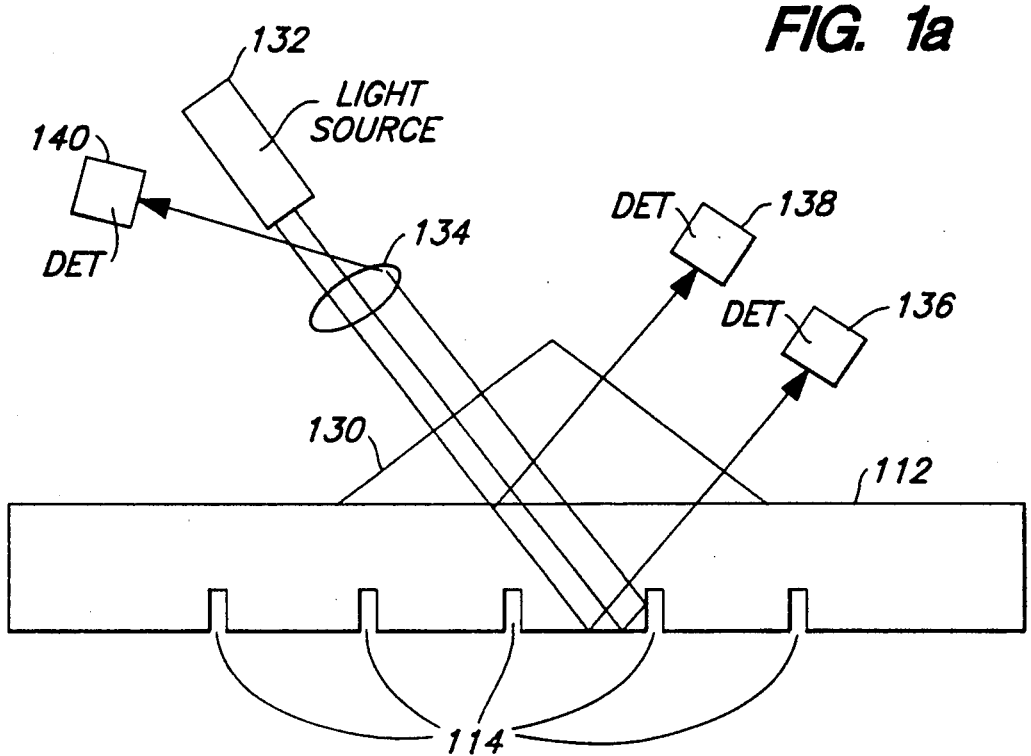
FIGS. 1a and 1b are elevation drawings of optical metrology instruments in accordance with the present invention.
Figure 1B:
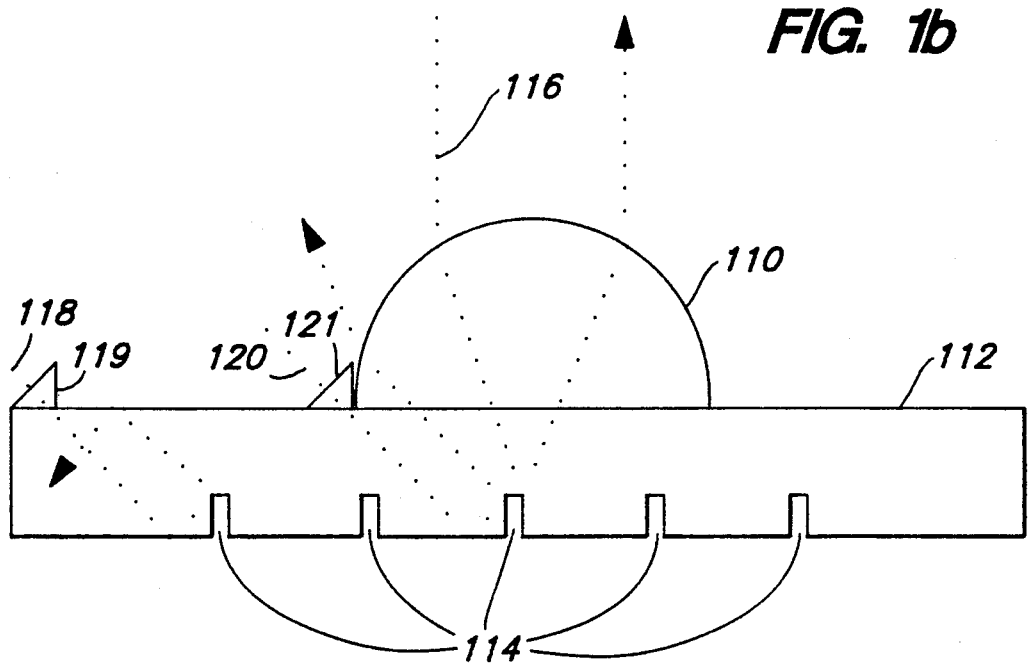

If, as shown in FIGS. 1a and 1b, a prism or plano-convex lens is held in intimate contact with the back surface of the wafer, acceptable separation (i.e. <50 nm) can be achieved. This is possible because semiconductor wafers as used in manufacturing are very smooth. The prism is used in the configuration shown in FIG. 1a, which is described below in more detail. The plano-convex lens is used as the objective lens of an infrared microscope in several configurations. While the discussion below concerning the coupling of the optical device to the wafer focuses on the lens application shown in FIG. 1b, it applies equally to the prism application shown in FIG. 1a.

The contact lens has advantages other than the relatively high resolution achieved due to the propagation of high-angle waves from the wafer into the air. Firm contact between the lens and the wafer suppresses vibration which may add noise components to interferometric measurements. In addition, this firm contact substantially eliminates mechanical creep and drift between the lens and sample. Since the thickness of most wafers is precisely known, a contact lens also facilitates the focusing of the image obtained from the wafer. In addition, this solution has advantages over using index matching fluid between the lens and the wafer since the contact lens eliminates the possibility of the wafer being contaminated by the indexing fluid.

A lens in contact with the wafer, however, does present two problems. First, if the surface of the wafer or the flat surface of the lens are not clean, the particles on the surfaces may hold the lens and wafer so far apart that good optical coupling is not achieved. Moreover, repeated contact between the lens and the wafer surface may damage the lens from frictional wear and from the imbedding of particles into the flat surface of the lens. This damage accumulates over time and can successively reduce the quality of the measurements made using the lens until the lens is unserviceable.

Second, When the objective lens is in contact with the wafer surface, it is difficult to navigate the microscope (i.e. to move the sample while viewing it, as is done with ordinary microscopes). Since the lens cannot be easily moved once contact has been made, it may be desirable to design the remainder of the microscope optics to provide a relatively large field of view. Alternatively, a low resolution image, generated from small angle rays which propagate through a relatively large air gap, may be used to navigate the objective lens to a desired position before contact is made. In this instance, it may be desirable to use a diaphragm above the lens to reduce the NA of the system appropriately.

These problems would be mitigated if the objective lens could propagate high-angle rays without being in contact with the surface of the wafer. In visible light microscopes, immersion lenses are sometimes used to achieve numerical apertures greater than unity. These microscopes use an index matching fluid (or fusible solid) to provide a continuous optical path from the top of the objective lens to the sample without any air-glass interfaces.

If this approach were used with the silicon objective lens described above, the requirement that the surfaces of lens and the wafer be very clean could be relaxed, since the fluid tends to conform the surface without gaps even if particles are present. In conventional visible light microscopes, the index matching fluid is selected to closely match the index of refraction of the glass lenses and cover slips. Consequently, all of the rays from the lens are propagating rays in the fluid and vice versa. Interfacial reflections are substantially eliminated.

Two considerations make this technique unworkable for the silicon and gallium arsenide lenses described above: the desirability of avoiding sample contamination and the lack of any convenient non-toxic fluids having refractive indices above 2.3 in the near-infrared.

There are, however, two variations on the index matching fluid technique which are applicable to the semiconductor lenses. The first variation is to coat the flat face of the objective lens with an easily deformed solid material, such as indium antimonide, which is transparent in the near-infrared and has a refractive index that is greater than three. High angle rays in silicon would couple well into such a material as either propagating or weakly evanescent waves. If the gap between the flat surface of the lens and the back surface of the wafer were filled with a substance of this type, the contact tolerance would be substantially relaxed. Small particles adhering to the lens or to the sample could imbed themselves under moderate pressure and, consequently, would not wedge the surfaces apart. While the coating would sustain damage over time, it could be dissolved away and a new coating applied to renew the lens.

A second variation is to reduce the numerical aperture of the objective lens somewhat, for example, to 2.7, and use one of several index matching fluids or fusible solids which have indices of refraction of about 2.3 in the gap. This solution is illustrated in FIG. 2b. The numerical aperture of the lens can be reduced, for example, by inserting a diaphragm 218 above the top surface of the objective lens to block the higher angle rays. An exemplary index matching oil is type J821X-2.11 which has a refractive index of 2.11. A fusible solid index matching material is available as type J833X-2.31 which has a refractive index of 2.31. Both of these materials are available from R. P. Cargille Laboratories, Inc. Since these materials do not match the index of refraction of the silicon, they are not properly called index matching materials. Thus, these materials are referred to hereafter as "optical coupling materials."

If this technique were used, some of the light passing through the interface would be weakly evanescent. Good coupling of infrared rays could be maintained, however, by positioning the lens mechanically so that only a relatively thin layer of fluid exists between the lens and the wafer. Using this technique the evanescent waves in the fluid are converted to propagating waves through frustrated total internal reflection. This represents a fundamental difference from conventional index matching techniques since, in conventional index matching microscopes, evanescent waves are avoided.

The vertical positioning mechanism used with the exemplary optical coupling materials would exhibit greater tolerance to positioning errors than a positioning mechanism which attempts to maintain an air separation of 30 nm to 50 nm between the lens and the wafer without using an optical coupling fluid.

An alternative high-tolerance positioning mechanism, which does not rely on the optical coupling materials described above, is shown in FIG. 2d. This mechanism employs an air bearing similar to those used to hold recording heads which "fly" over the surface of the magnetic disk at a height of about 50 nm. The air bearing used in this embodiment of the invention maintains a spacing of between 30 nm and 50 nm between the bottom of an assembly including the lens and the assembly and the back surface of the wafer.

The exemplary air bearing includes an relatively thin silicon wafer 112' which physically attached to the lens. This assembly has nozzles 220 which are coupled to ducts 218 around the circumference of the lens. The exemplary ducts end in small holes (not shown) in the bottom surface of the bearing assembly 112'. Air enters the nozzles 220 and follows the path illustrated by the arrows 222. Alternatively, the air bearing may be implemented in a lens of the type shown in FIG. 2c by using micro-machine techniques to drill holes (not shown) in the lens itself at positions around the circumference. Details on the implementation of an exemplary air bearing are contained in an article by K. J. Stout et al entitled "Externally Pressurized Bearings for Systems Leading to Nanometer Technology" in "Scanning Microscopy Technologies and Applications", SPIE Proc. Vol. 897, pp 144–153 which are hereby incorporated by reference.

Two applications in which an optical device is in intimate contact with the back surface of the wafer are illustrated in FIGS. 1a and 1b. In FIG. 1a, a silicon prism 130, which may, for example, be incorporated into the wafer chuck of reactive-ion etching apparatus, is held in contact with the back surface of silicon wafer 112. The wafer 112 includes trenches 114 which are being formed by reactive ion etching. A source 132 of infrared light, for example, a 1.3 $\mu$m laser diode or light-emitting diode (LED), is configured to emit a relatively narrow beam of infrared light which is directed, through a lens 134, to one facet of the prism 130. The angle of incidence for the light is chosen so that total internal reflection of the light occurs both at the front surface of the wafer and at the trench walls.

Three infrared detectors, 136, 138 and 140 are configured to collect three different types of reflected light. Detector 136 collects the light reflected from the front surface of the wafer and detector 138 detects the light reflected from the prism-wafer interface. Detector 140 is positioned to receive light reflected from the trench walls.

In the absence of surface features, all light provided by source 132 is reflected specularly from the front surface of the wafer of from the wafer-prism interface. This light exits through the opposite facet of the prism 130 onto the detectors 136 and 138, respectively. A trench or an array of trenches, however, acts as a corner reflector, causing some of the light to be reflected back through the first prism facet, through the lens 134 and onto the detector 140.

Since the trenches 114 are deep compared to a wavelength of the infra-red light (400 nm in silicon), a plot of the strength of the corner reflection does not exhibit pronounced ripples as the trench grows deeper. If the numerical aperture of the focussed beam is chosen to be large enough that any interference fringes caused by the spacing of the trenches are averaged out, but not so large that the trenches are illuminated nonuniformly, then the strength of the reflected signal is a monotonic function of trench depth.

The detectors 136 and 138 ensure that the measuring device is operating properly and provide signals which may be used to normalize the signal provided by the detector 140. If there is poor contact between the prism 130 and the wafer 112, less light energy than normal is transmitted through the wafer-prism interface, resulting in a smaller than normal signal from detector 140. In this instance, however, the signal from detector 138 is larger than normal.

The signal from detector 138 may be used as a simple error indicator signal or as a control signal to determine a correction factor to be is applied to the signal from detector 140 to mitigate errors arising from poor contact.

The signal from detector 136 serves as a comparison signal for the signal from detector 140. The ratio of these two signals provides a normalized reflectance for trench corners. This signal may be used to control the reactive ion etching process by setting a threshold for the ratio of the signals from the detectors 140 and 138 indicating a desired trench depth. When the measured ratio exceeds the threshold, the reactive ion etching operation may be stopped.

FIG. 1b illustrates the basic idea of a silicon objective lens 110 in intimate contact with a silicon wafer. As illustrated by ray 118, which is coupled into the wafer via a prism 119, light entering the wafer at an angle greater than the critical angle is totally internally reflected. High angle rays reflected, for example by a trench 114 acting as a corner reflector, cannot propagate out of the wafer 112. When, however, a ray 120 is coupled into the wafer by a silicon prism 121 which is positioned close to the lens 110, the reflection of the ray 120 from the trench 114 is converted, by the lens 110, into a ray which propagates in air.

The structure shown in FIG. 1b serves as the basis of a high NA infrared microscope. There are, however, several disadvantages of this structure. First, since the lens is in contact with the wafer, it is difficult to navigate the microscope as described above. Second, since the lens is desirably kept in close proximity to the wafer surface, its focal point cannot change significantly.

Figure 3:
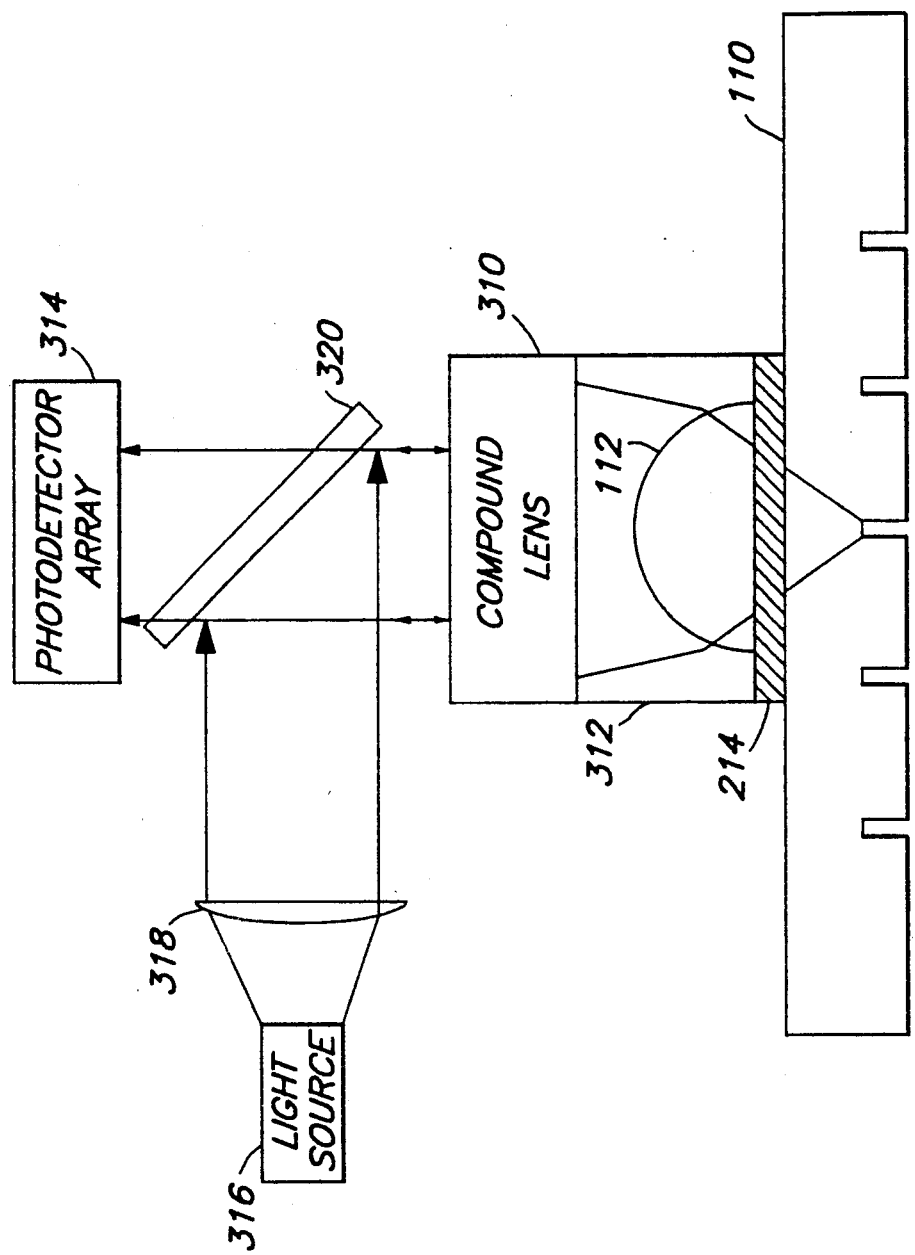
FIG. 3 is an elevation drawing of an infrared microscope which includes the instrument shown in FIG. 1b.

FIG. 3 illustrates a practical bright-field infrared microscope which may be used for wafer inspection. In this microscope, the hemispherical silicon lens 112 is combined with a compound lens 310 to form a variable focus lens structure 312. The lens structure 312 floats above the surface of the wafer 110 on a thin layer of optical coupling fluid 214. The focal point of the microscope is adjusted by changing the positions of the elements of the compound lens 310 relative to the lens 112 in the manner of a conventional zoom lens. For the sake of simplicity, the apparatus for adjusting the compound lens elements is not shown.

In FIG. 3, a light source 316 provides infrared light to a collimating lens 318. The lens 318 and light source 316 define a the illumination function for the microscope. As used herein, the term "illumination function" indicates the actual incident light field at the sample. A related term is the "image function." As used herein, this term defines the image field distribution obtained from the microscope. Another related term is "pupil function." As used herein, the pupil function is the coherent transfer function of the microscope. It is the two-dimensional optical Fourier transform of the point spread (impulse) function of the microscope. There is a Fourier transform relationship between the pupil of a microscope and the object and image planes. A point source in the pupil produces a plane wave at the object/image and vise-versa. If the pupil function is multiplied by the complex reflection coefficient of the sample, the result is the optical Fourier transform of the image.

Light from the lens 318 is partially reflected by a beam splitter 320 onto the wafer 112 through the variable focus lens 312. Light reflected from the front surface of the wafer passes through the beam splitter 320 to a conventional infrared photodetector array 314 which lies in the image plane of the lens system 312.

It is contemplated that the microscope shown in FIG. 3 may be modified in several ways. First, the compound lens 310 may be replaced by a single lens, such as a meniscus lens (not shown). The focal point of the combination of the combined lenses may be changed by moving the meniscus lens relative to the fixed lens 112. This lens combination, however, is inferior in image quality, field flatness and field of view compared to the variable focus lens 312 shown in FIG. 3.

Using the bright field microscope, most of the light is totally internally reflected (i.e. back through the lens 112) at the top surface of the wafer. There is, however, significant scattering of light at discontinuities in the top surface. The edges of dielectric films (e.g. oxide traces or photoresist) or trench walls cause significant coupling of high-angle rays (which would normally be totally internally reflected) into low-angle waves which can propagate through the top-surface silicon-air interface. These discontinuities appear dark in the bright field image.

If the illumination function includes low-angle as well as high-angle rays, dielectric films appear darker throughout, not just at the edges. This occurs because, due to the high refractive index, more light can propagate through the boundary. Much of this light is coupled into leaky waveguide modes in the dielectric film and, so, eventually returns to be collected by the microscope. Some light, however, is scattered into the air, leading to darkening of the image in the regions covered by the films.

The interference between light returning from the leaky waveguide modes and the specularly reflected light may cause fringes and other artifacts if steps are not taken to prevent it. Metal reflectors may appear dark, since they absorb some of the incident light. Trenches may have a very complicated appearance due to interference between various scattered components, both in and out of focus. Nonetheless, the bright field microscope may be very useful for measuring the width of the bottoms of photoresist, oxide and other dielectric films.

Figure 4A:
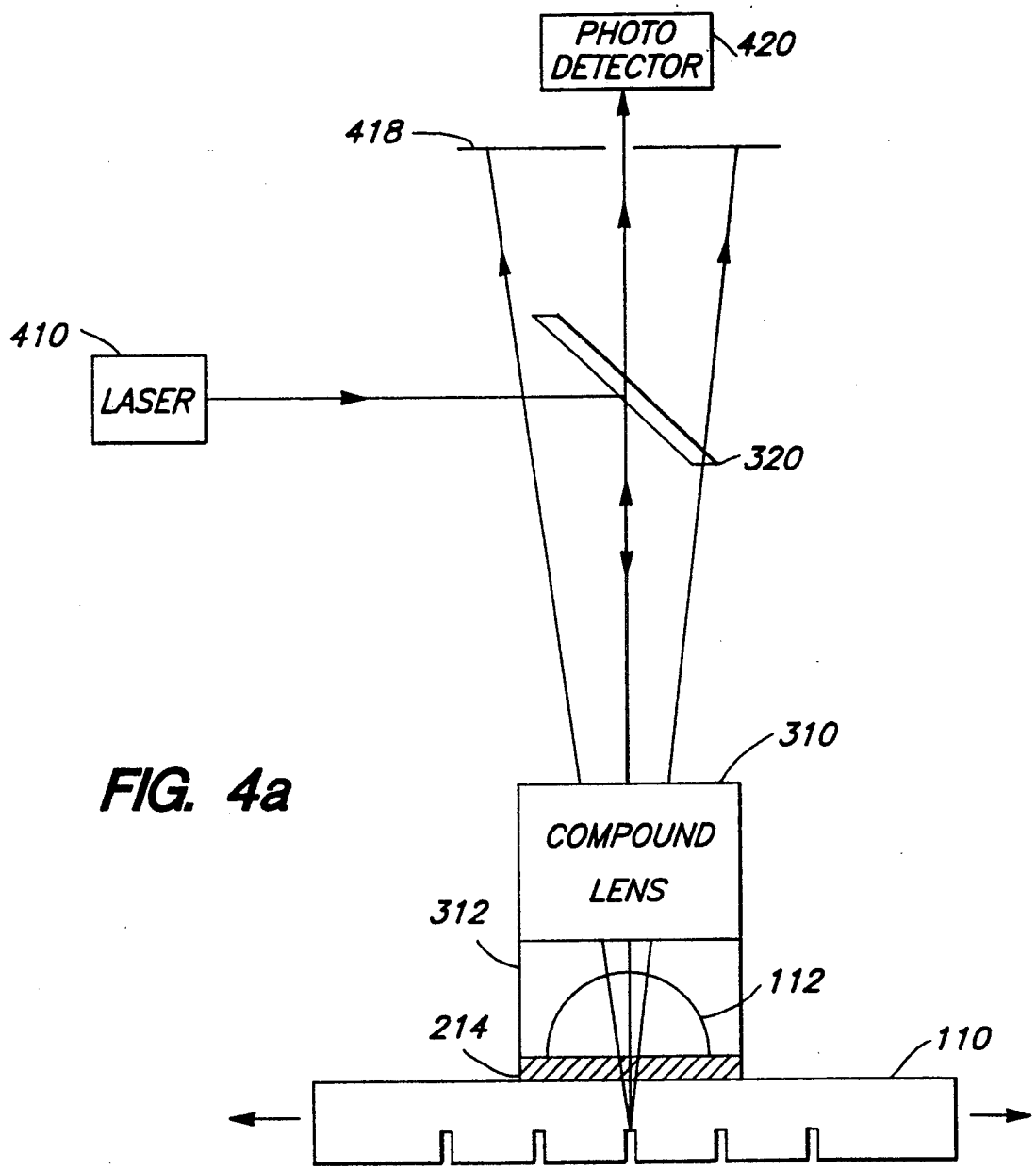
FIGS. 4a through 4i are elevation drawings, partly in block diagram form of various optical instruments which are based on the instrument shown in FIG. 1b.

A relatively simple variation on the bright field microscope is the confocal intensity microscope shown in FIG. 4a. The general principles of confocal intensity microscopes are described in U.S. Pat. No. 3,013,467 to M. Minsky entitled MICROSCOPY APPARATUS which is hereby incorporated by reference for its teachings on confocal intensity microscopes.

In the device shown in FIG. 4a, the light source 316 is replaced by a laser 410 and a pinhole 418 is placed in front of a single photodetector 420 at the image of the scanned spot. The other components of the microscope are the same as in FIG. 3.

There is one difference, however, in the use of the microscope, since the output is a single beam of light, the microscope is scanned across the wafer to develop an image. In order to maintain the alignment between the pinhole 418 and the image of the laser reflected through the variable focus lens 312 and beam splitter 320, the components of the microscope are maintained in a fixed position and the wafer 110 is moved beneath it to effect the scanning operation. Thus, a complete confocal microscope would include positioning apparatus (not shown) which would move the wafer in a reasonable manner along the x-coordinate direction (across the page) and the y-coordinate direction (out of the page). The juxtaposed sample points detected by the photodetector 420 at each position would form a complete image.

The major advantages of this approach over the bright field microscope described above include depth discrimination (optical sectioning), speckle reduction, and the rejection of waveguide effects in thin dielectric films. The depth discrimination property arises from the inability of light from out-of-focus levels of the sample to pass through the pinhole to the detector. This property allows the depth of trenches and other trench features to be measured. Indeed, this microscope can obtain cross-sectional images of the trenches at various levels, without interference from blurred images at other levels.

Depth measurement in this mode is relatively simple. At each trench, the focus is swept from the top of the trench to its bottom. Each reflecting plane causes a distinct maximum in the signal as the focus is swept through it. Depth may be obtained by subtracting the z coordinate of the front surface of the wafer from that of the trench bottom.

The waveguide rejection effect leads to improved images of dielectric lines, since the radiation from the leaky waveguide modes largely misses the pinhole on the return path. Thus, this component of the reflected light does not confuse the image. Measurement of dielectric films on the top surface is also improved in this mode. A dielectric film introduces spherical aberration into the reflected beam, due to the different phase changes on total internal reflection of different plane wave components. If the pupil function has no components which can propagate in the film, the darkening in the resulting image is independent of the thickness of the film.

Besides bright field and confocal imaging, two other types of intensity imaging are possible using the contact microscope. Among these are the Schlieren microscope, described below with reference to FIG. 4b; a conventional dark-field microscope described below with reference to FIG. 4c; and a dark-field transmission microscope, described below with reference to FIG. 4d.

In microscopes of these types, where light from the illuminator and from the object may be treated differently in their respective transform (pupil) planes, it is useful to distinguish between a "transmit" pupil function and a "receive" pupil function. The transmit pupil function includes the Fourier transform of the illumination function and the receive pupil function includes the Fourier transform of the image function. Depending on the optical system, the two pupil functions may or may not be in the same position.

An exemplary Schlieren microscope is shown in FIG. 2b. The Schlieren system is configured to have disjoint transmit and receive pupil functions (i.e. no area in common). A pair of knife edges are used as spatial filters, one masking a portion of the transmit pupil plane and the other masking a portion of the receive pupil plane. The knife edges are arranged so that the respective masked portions nearly overlap (bright Schlieren) or overlap slightly (dark Schlieren). The detected image is largely composed of light which has been scattered from positive to negative spatial frequencies. Assuming the knife edges to be parallel to the y axis, only light which has had the component of its wave vector, k, in the plane of the surface converted from the positive x direction to the negative x direction is detected.

Figure 4B:
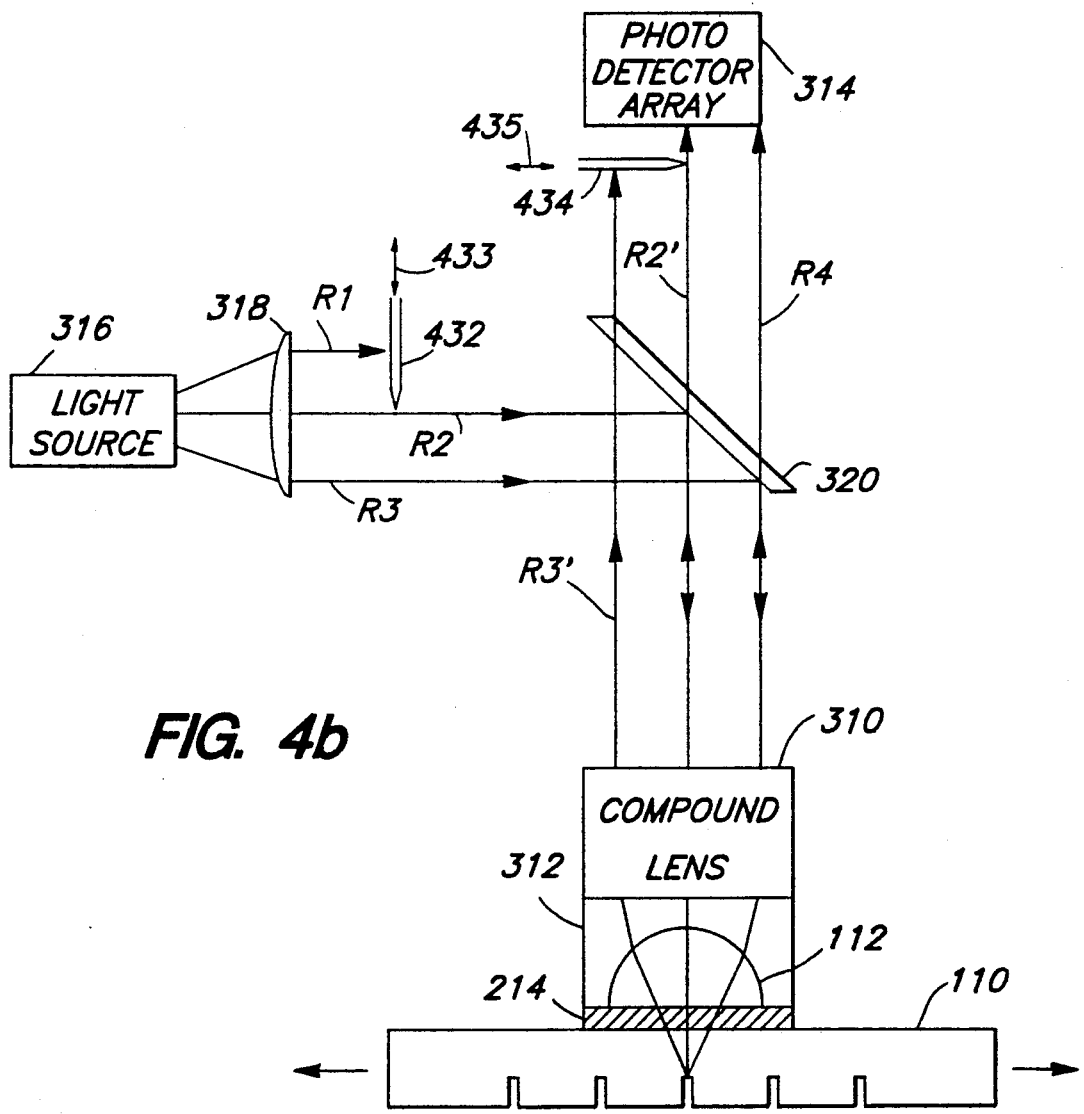

The apparatus shown in FIG. 4b is the same as that shown in FIG. 3 with the addition of two knife edges 432 and 434. The knife edges may be moved as indicated by the arrows 433 and 435 to implement either the bright-Schlieren or dark-Schlieren modes of operation.

The operation of the microscope is may be described in terms of rays R1, R2 and R3 generated by the light source 316. As shown in FIG. 4b, ray R1 is blocked by the knife edge 432 while rays R2 and R3 are allowed to propagate to the beam splitter 320. The components of rays R2 and R3 which are reflected from the beam splitter 320 enter the variable focus lens assembly, are reflected from the surface of the wafer 110 and emerge as rays R2' and R3'. In addition, components of R2 and R3 which have been scattered from positive to negative spatial frequencies, for example, by reflection from a trench wall, are produced. These rays are represented by R4.

Rays R2', R3' and R4 pass through the beam splitter 320. Ray R3' is blocked by the knife edge 434 while rays R2' and R4 form an image on the photo detector array 314. The configuration shown is the bright-Schlieren mode. If one of the knife edges 432 or 434 is moved to block either ray R2 or ray R2' the apparatus would be configured in the dark-Schlieren mode.

The Schlieren modes are particularly adapted to trench measurements, since the sides of the trenches meeting the top wafer surface form a corner reflector, which scatters light backwards in x very efficiently.

When the light source 316 and lens 318 are replaced by a laser, the confocal imaging technique of FIG. 4a is implemented in the Schlieren microscope. This may also be done, for example, by inserting a spatial filter consisting of a pinhole (not shown) at the focus of a lens which is positioned between the knife edge 434 and the photo detector array 314. The image is formed by scanning the wafer 110. The resulting instrument would be very effective for measuring trench depth. In operation, if the microscope were positioned directly over a trench 114, the image would become almost completely dark when the focus is scanned up past the trench bottom. In addition, trench side wall angle can be measured directly by measuring image intensity as a function of the overlap of the two knife edges. Vertical side walls would produce scattered field components in which $k'_x = -k_x$ where $k_x$ is the transverse wave vector of the incident plane wave component and $k'_x$ is that of the reflected component. Non-vertical side walls may result in $k'_x + k_x \neq 0$. This shift may be measured by changing the overlap of the knife edges 432 and 434.

Dark field imaging using the high NA microscope may be done either in reflection or transmission. The basic idea behind dark-field microscopy is to choose an illumination function such that no light from the illumination function may propagate specularly into the image. This may be done, for example, by spatially filtering the pupil function with a first filter (mask in the transmit pupil plane) and by spatially filtering the image function with a second filter (mask in the receive pupil plane). For a dark field microscope, the light passed by the transmit pupil mask as imaged from a featureless wafer is entirely blocked by the receive pupil mask.

Figure 4C:
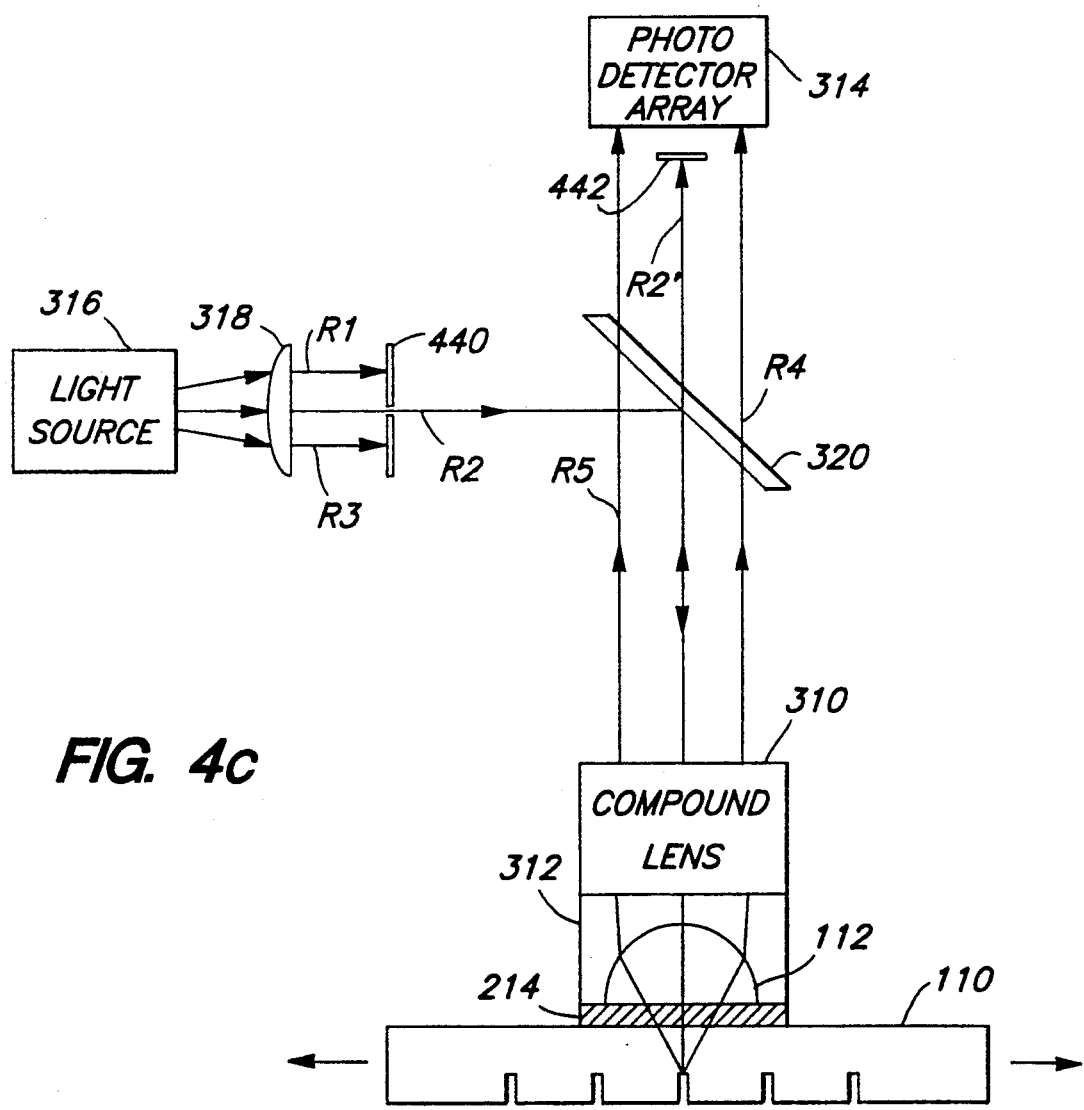

Apparatus for performing reflection dark field microscopy is shown in FIG. 4c. This apparatus differs from the microscope shown in FIG. 3 by the transmit pupil mask 440 and receive pupil mask 442. As shown in FIG. 4c, the transmit mask 440 is a pinhole which passes only ray R2, blocking rays R1 and R3. Ray R2 is then partially reflected by beam splitter 320 into the variable focus lens 312. Reflection from the front surface of the wafer 110 specularly reflects ray R2' and scatters rays R4 and R5. All of these rays pass through the variable focus lens, and through the beam splitter 320. Ray R2', however, is blocked by receive pupil mask 442 before it can reach the photo detector array 314. Rays R4 and R5 propagate to the array 314 and provide the dark-field image.

In this configuration, a featureless sample will produce a completely dark image since all components of ray R2 will be reflected back as ray R2'. Any discontinuity in the front surface of the sample appear on the image as bright light on a black background.

An interesting dark field microscope (not shown) is obtained when the transmit pupil mask 440 and the receive pupil mask 442 of FIG. 4c are switched and a laser is employed as the light source, as shown in FIG. 4a. The resulting microscope rejects rays reflected from smooth vertical trench walls. These rays are back-reflected into the region of the pupil occupied by the illumination due to the corner reflector formed by the trench walls and the front surface of the wafer. Thus, irregularities in the trench walls, such as voids, pinholes or contamination in the trenches appear as bright areas on a relatively dark background. In addition, since the mask 440 is a pinhole and only one spot on the sample is illuminated, this exemplary microscope is a confocal imaging device, and thus, is relatively immune to interference from out-of-focus layers or from waveguide propagation modes in dielectric films on the surface of the wafer. Another advantage of the confocal configuration is depth discrimination. As described above, due to the rejection of interference from out-of-focus layers, the depth of a feature in the wafer may be obtained by adjusting the variable focus lens 312 to different focal points on a line perpendicular to the faces of the wafer 110.

Figure 4D:
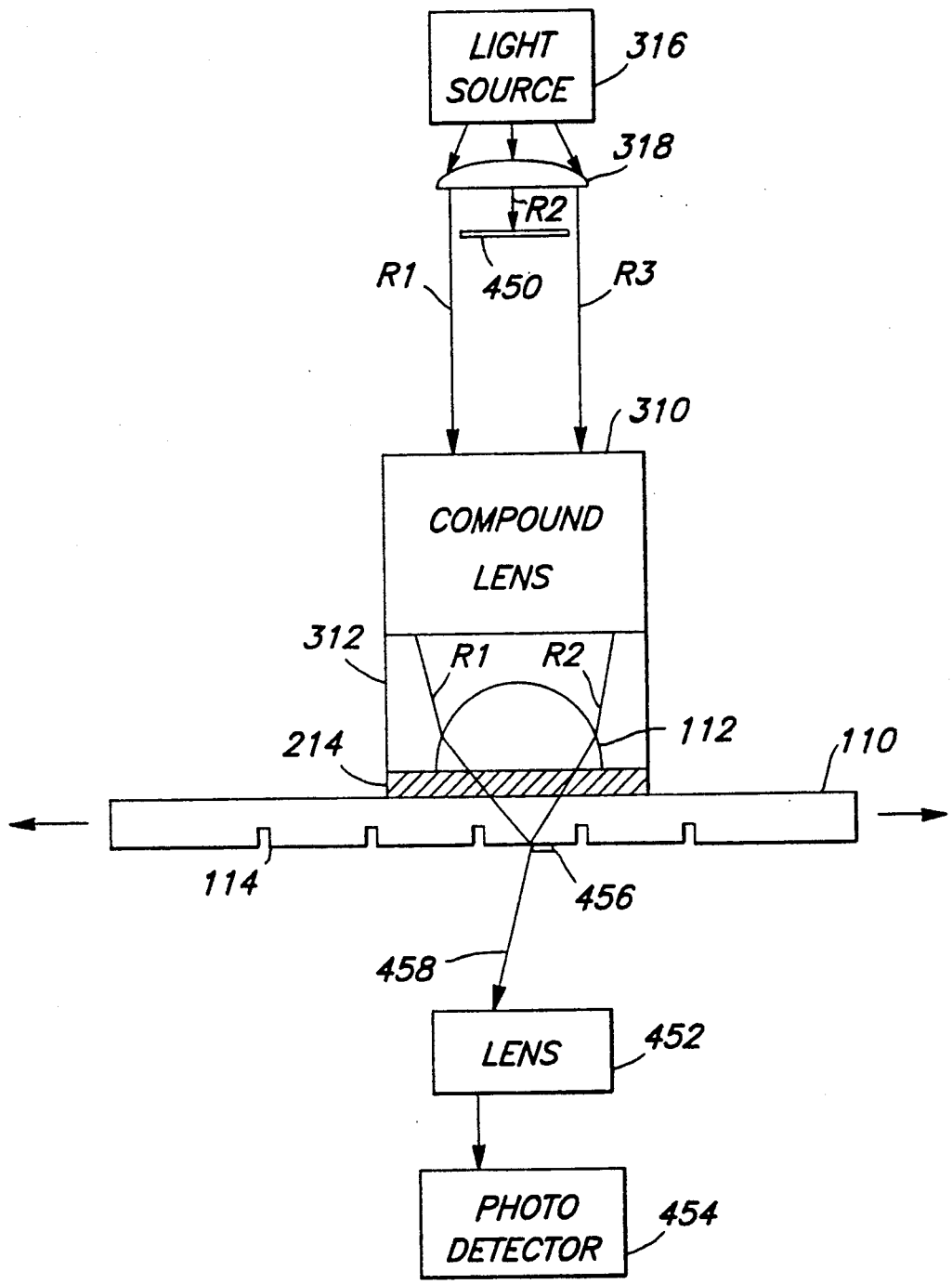

FIG. 4d is an elevation view of an exemplary dark field transmission microscope. The principle behind this instrument is to select an illumination function that excludes all components which can propagate from the wafer in air. A detector positioned outside the top surface of the wafer detects only that light which is scattered from evanescent to propagating modes by discontinuities in the top surface.

As shown in FIG. 4d, the dark-field transmission microscope includes a light source 316 and collimating lens 318 which produce, for example rays R1, R2 and R3. R2 and other rays in the center portion of the pupil plane are blocked by a pupil mask 450 so that only the outer rays of the pupil plane, R2 and R3 propagate to the variable focus lens 312. In the lens 312, the outer rays R2 and R3 are converted, by the compound lens 310, into high-angle rays which are coupled into the wafer 110 through the high-NA lens 112 and the optical coupling fluid 214.

Inside the wafer 110, these rays are at angles greater than the critical angle and, so, are subject to total internal reflection. Rays 458 may only propagate through the top surface, of the wafer through a lens 452 and onto a photodetector 454 if the high-angle rays are converted into propagating rays. This conversion may occur, for example, when a high-angle ray is reflected from a discontinuity in the surface, such as the wall of a trench 114, or when a dielectric film 456, such as $SiO_2$ or photoresist, scatters the non-propagating rays into propagating rays.

An image of the wafer may be obtained by holding the light source 316, lens 312 and detector 454 in fixed positions while the wafer is moved incrementally in both the x (across the page) and y (out of the page) directions.

The discussion above has encompassed imaging techniques which utilize the high-NA lens as a component in a conventional imaging microscope. Because very little light can couple from the front surface of the wafer into the air, many measurement techniques based on phase and polarization shifts of the totally internally reflected light are possible. Generally both heterodyne and homodyne interferometers are used to measure optical phase. Several types of interferometers are described below with reference to FIGS. 4e through 4g.

Interferometers can be divided into three types: one-beam, two-beam and multiple beam. One beam systems include Zernike and Corle-Kino interferometers. In a one-beam system, one part of the pupil function is phase shifted with respect to the other and the images resulting from the two regions are either summed and squared, as in a Zernike system, or multiplied together (heterodyned) using alternating current (AC) detection, as in a Corle-Kino system.

An exemplary Corle-Kino interferometer (not shown) may be built by placing an AC driven phase plate in the pupil plane of a confocal microscope, such as that shown in FIG. 4a. Using a Corle-Kino interferometer, both amplitude and phase can be measured simultaneously. This device allows single-beam phase sensitive imaging of the inside of a wafer and of features in contact with the wafer. Due to the relatively small range of phase shifts that can be accommodated by this device, it may not be appropriate for measuring image features which go far out of focus. Details on Zernike phase contrast, upon which both of the single-beam interferometers are based, may be found in a book by M. Born et al entitled *Princicles of Optics,* 6th ed. Pergamon, (1980), which is hereby incorporated by reference.

An exemplary multiple-beam interferometer which may be developed for use with the high NA lens is a Fabry-Perot interferometer. An interferometer of this type (not shown) may be built by placing a highly reflecting coating on the curved surface of the lens 112 shown in FIG. 1b. The center of curvature of the spherical surface is in the plane of the top surface of the wafer. Consequently, the coated back surface of the lens forms a spherical resonator with the front surface of the wafer. The finesse of the cavity depends on the reflectivity of the front surface and on the optical absorption of the wafer under test (which may be relatively large for a heavily doped substrate).

Amplitude may be sensed by measuring the finesse of the resonator (high absorption→low finesse, high reflectance→low finesse). This may be done, for example, by frequency modulating the light source and measuring the corresponding change in the reflected signal. For a fixed frequency deviation, the AC signal is proportional to the finesse of the cavity.

Phase changes on reflection from the wafer surface cause corresponding changes in the resonance wavelength, which, in turn, cause changes in the reflectance of the front surface of the wafer. Performing phase measurement using the baseband signal and the amplitude measurements using a relatively high modulation frequency allows the two components to be separated.

Since the cavity is desirably solid, it may be necessary to adjust the operating point by tuning the illumination wavelength. This may be done, for example, by using a 1.3 μm laser diode as the illuminator. The wavelength of the light produced by a laser diode can be adjusted by changing its drive current. As the lens or beam is scanned over the sample, irregularities in topography or changes in the index of refraction of dielectric films on the front surface of the wafer 110 cause phase changes on reflection, changing the optical length of the cavity and, so, changing the absorption of the cavity. If the laser wavelength is servo-controlled, the servo voltage may be used as the measurement data. Otherwise, the output signal is taken from a photodetector (not shown) and the signal is proportional to the total reflection.

Exemplary two-beam interferometers include the Michelson, Mach-Zehnder, Linnik, Mirau, Twyman-Green and Nomarski systems, all of which can be implemented in both homodyne and heterodyne versions using the high-NA lens. For the sake of brevity, only two variants of the Linnik interferometer are described below with reference to FIGS. 4e and 4g.

Figure 4E:
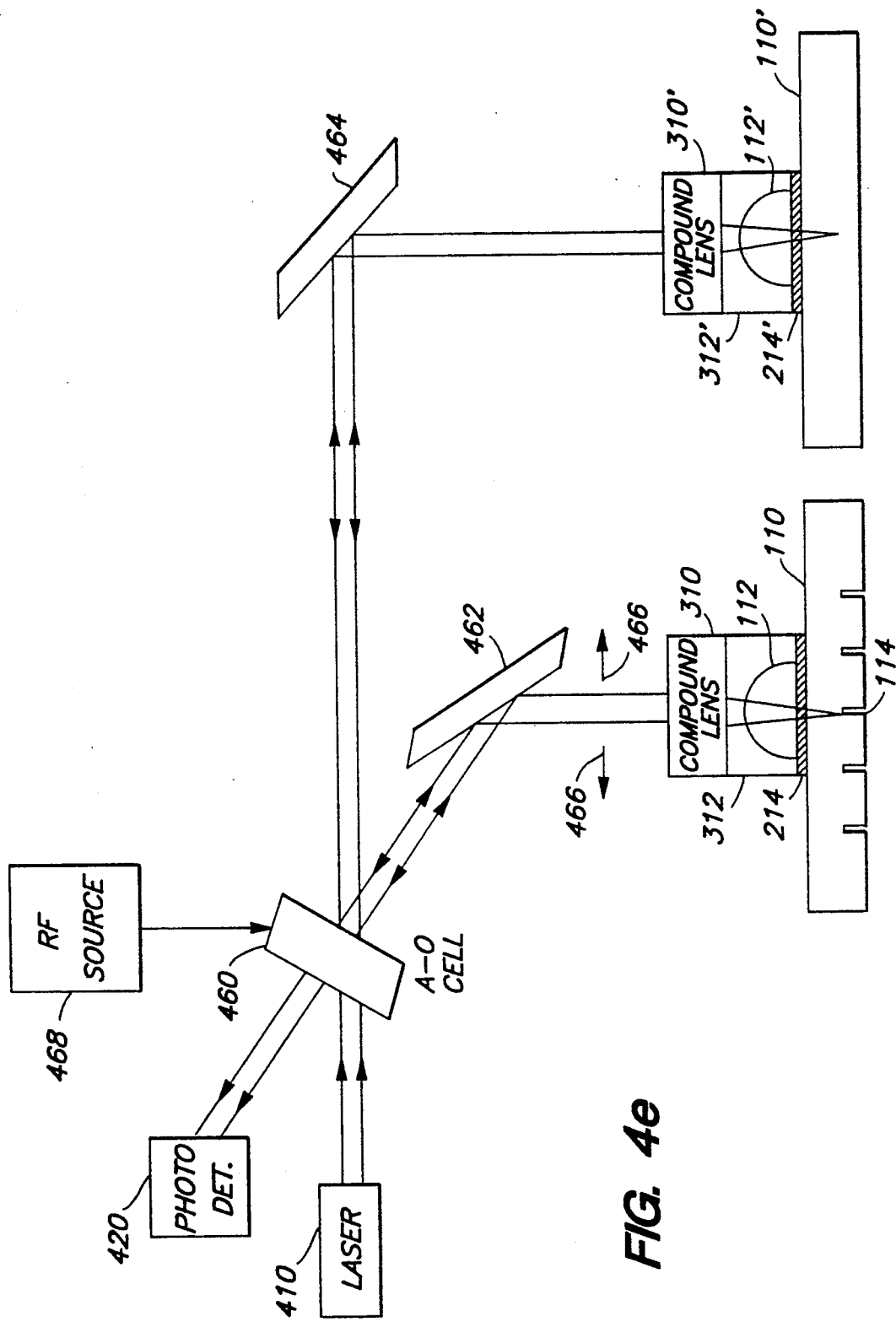

FIG. 4e is an elevation view of an exemplary Linnik interferometer. The Linnik system is a Michelson two-arm interferometer in which identical lenses have been placed in front of the mirrors (i.e. wafers) on each arm. In a practical implementation using the high NA lens system, each arm has an identical lens system and the reference arm has a blank wafer coupled to its lens system to allow operation with wafers of various thicknesses.

The Linnik interferometer may be implemented either as a homodyne system or as a heterodyne system. An exemplary heterodyne implementation is shown in FIG. 4e while a modified homodyne implementation is shown in FIG. 4g, described in more detail below.

In a high-NA system operating inside dielectric materials (e.g. water, glass or silicon), the image reflected from a dielectric interface may be aberrated due to the phase shift which occurs on total internal reflection. This phase shift varies from 0 to $\pi$ radians as the angle of incidence increases from the critical angle $\Theta_i = \Theta_c$ to grazing, $\Theta_i = \pi/2$. Part of the aberration can be compensated for by shifting the focus of the microscope. The remainder, however, may cause a significant degradation of the quality of the image produced by the microscope. For semiconductor inspection, it is desirable for the resolution of the imaging system to be as close to ideal as possible. Consequently, the correction of this aberration is of great interest. Due to the unusual form of this aberration, it may be difficult to correct using conventional lens design techniques. One method by which the effect of this aberration can be substantially eliminated by designing the optical system as a two-beam heterodyne interferometer. In a system of this type, both the sample beam and the reference beam experience total internal reflection under substantially the same circumstances. The phase shift resulting from this reflection is substantially canceled, therefore, when the two beams are mixed for heterodyne detection.

In the system shown in FIG. 4e, light from a laser 410 is passed through an acousto-optic (AO) cell 460. In the exemplary embodiment, the AO cell may be a $TeO_2$ Bragg cell. A partial diffraction grating is established inside the cell 460 responsive to an acoustic signal provided by RF source 468.

In this configuration, the AO cell 460 deflects a portion of the incoming light by an angle determined by the frequency of the signal provided by the RF source and passes the remainder of the incoming light undeflected. The amount of light passed depends on the strength of the RF signal. In the exemplary embodiment of the invention, the signal from the RF source 468 ranges between frequencies of 60 MHz and 110 MHz and the strength of the RF signal is regulated so that half of the incoming laser beam is deflected and half is passed undeflected.

The deflected beam from the AO cell 460 is reflected from a front-surface mirror 462 into a variable focus lens 312 which is coupled to the back surface of a sample wafer 110 by a layer of optical coupling fluid 214.

The undeflected beam from the AO cell 460 is reflected from a mirror 464 into a variable focus lens 312' which is substantially identical to the lens 312. The lens 312' is coupled to the back surface of a reference wafer 110' by a layer of coupling fluid 214' having substantially the same thickness and composition as the layer 214.

Light reflected from the sample wafer 110 and from the reference wafer 110' travels back along the same path as the illuminating light. Upon reaching the AO cell 460, a portion of the reference beam is deflected onto a photodetector 420 and a portion of the sample beam is passed undeflected by the AO cell 460 onto the photodetector 420. At the photodetector 420 the two beams interfere producing both AC and DC photocurrent components.

The AC photocurrent components are the result of a heterodyne combination of the reflected sample and reference beams. Since the AO cell shifts the deflected wave in frequency by the frequency of its driving signal, and, since each of the waves incident upon the photodetector 420 has been deflected once by the AO cell 460, the phase of the beat between the reflected sample and reference beams is substantially equal to the phase difference between the beams which is caused by the difference in the reflective properties of the sample and reference wafers.

The Linnik interferometer shown in FIG. 4e is a confocal system even though it lacks pinholes, due to the coherence of the laser light and the optical superposition of the two spots, which multiply together to yield the beat signal. It may be scanned in the x direction across the wafer by the AO deflector 460, as indicated by the arrows 466. It may be scanned in the y direction (out of the page) by physically moving the sample wafer beneath the variable focus lens 312. Finally, the focus of the lens systems 312 and 312' may be racked from their maxima to their minima to perform a scanning of the wafer in the z direction (up and down the page).

It is contemplated that the Linnik interferometer shown in FIG. 4e may be used in a Schlieren mode by adding knife edges in the pupil and image planes as described above in reference to FIG. 4b. Alternatively, the interferometer may be configured in a dark field mode, as described above in reference to FIG. 4c. In either of these two modes, the Linnik interferometer may be used to measure trench sidewall angle, wall profile as well as inclusions, pinholes and voids in the trench walls or in the bulk semiconductor. Trench depth (height from the back surface) may be measured either in dark field modes or in bright field modes. The Linnik interferometer may also be used to measure the width and complex refractive indices of photoresist and other dielectric features deposited on the front surface of the wafer by measuring the phase shift on total internal reflection from the interface between the dielectric and the front surface of the wafer.

In addition to the above, the signals produced by the interferometer may be subject to digital filtering to transform the coherent transfer function of the instruments in ways that effectively achieve entirely new contrast systems. The filtering techniques employed are only subject to the numerical aperture of the lens system (spatial frequency bandwidth) and the field of view (which limits the length of practical filters). These techniques are described in a paper by P. C. D. Hobbs and G. S. Kino entitled "Generalizing the Confocal Microscope Via Heterodyne Interferometry and Digital Filtering" *Journal of Microscopy*, Vol 160, Pt. 3, December, 1990 pp 245-264, which is hereby incorporated by reference for its teachings of these techniques.

The structure and operation of the exemplary Linnik interferometer shown in FIG. 4e is similar to that of a phase sensitive scanning optical microscope described in an article by R. L. Jungerman et al. entitled "Phase Sensitive Scanning Optical Microscope" Appl. Phys. Lett. Vol. 45, No. 8, October 1984, pp 846-848 which is hereby incorporated by reference for its teachings in the design of a scanning optical microscope.

In addition to its uses in microscopy and interferometry, the high-NA lens system may be used to perform various polarization measurements including measuring stress-induced birefringence in the bulk of the wafer, near trenches and vias, and in thin films grown or deposited on the top surface of the wafer. Spatially resolved ellipsometry, electrooptic effects in GaAs and other III-V compounds, and depolarization due to scattering from anisotropic features may also be determined by polarization measurements made using the high-NA lens system.

In general, these measurements may be made by using a highly polarized incident wave, with any of the imaging devices or interferometers described above, and passing the reflected or transmitted wave through an analyzer before it is detected.

Figure 4F:
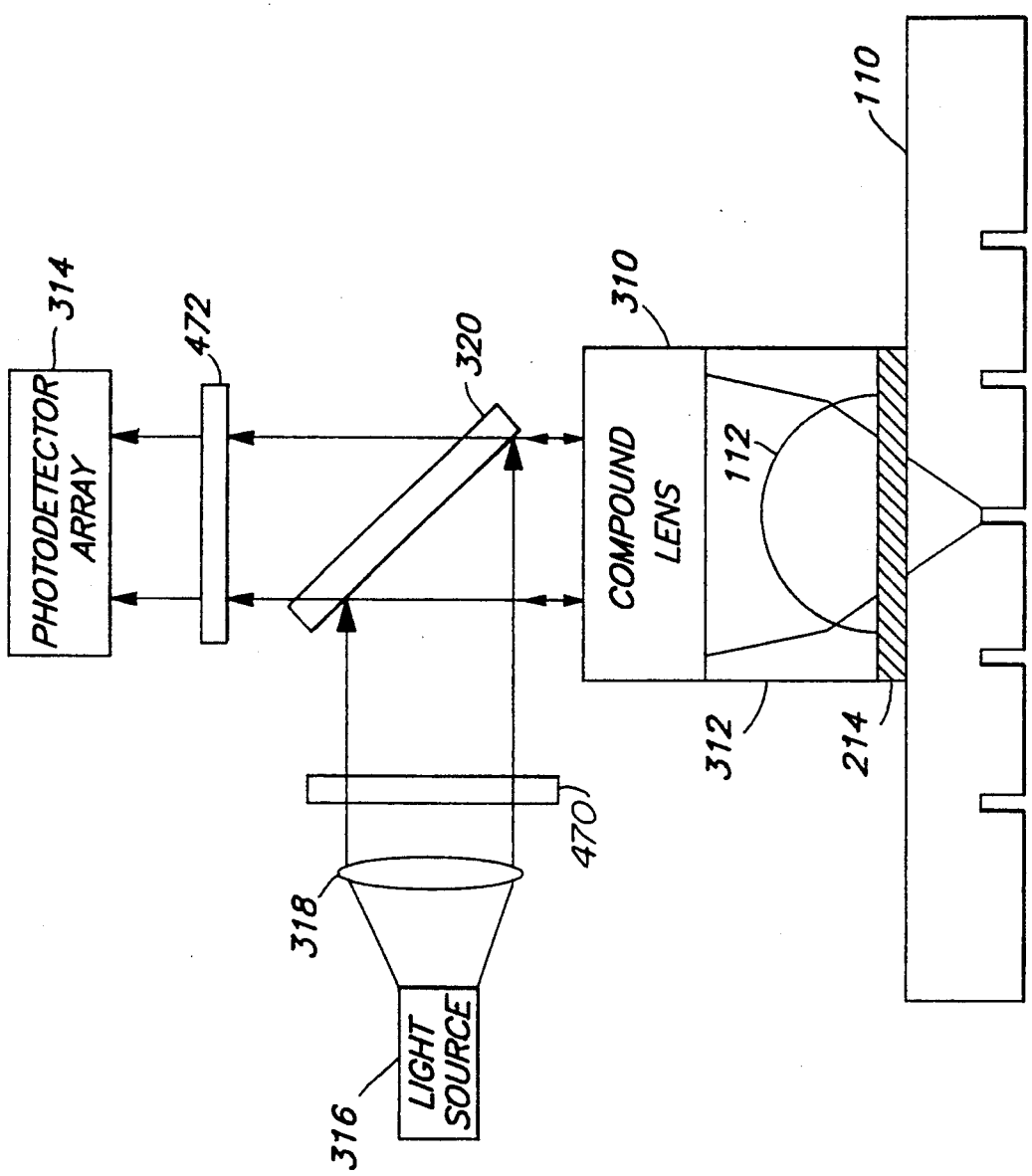
Figure 4G:
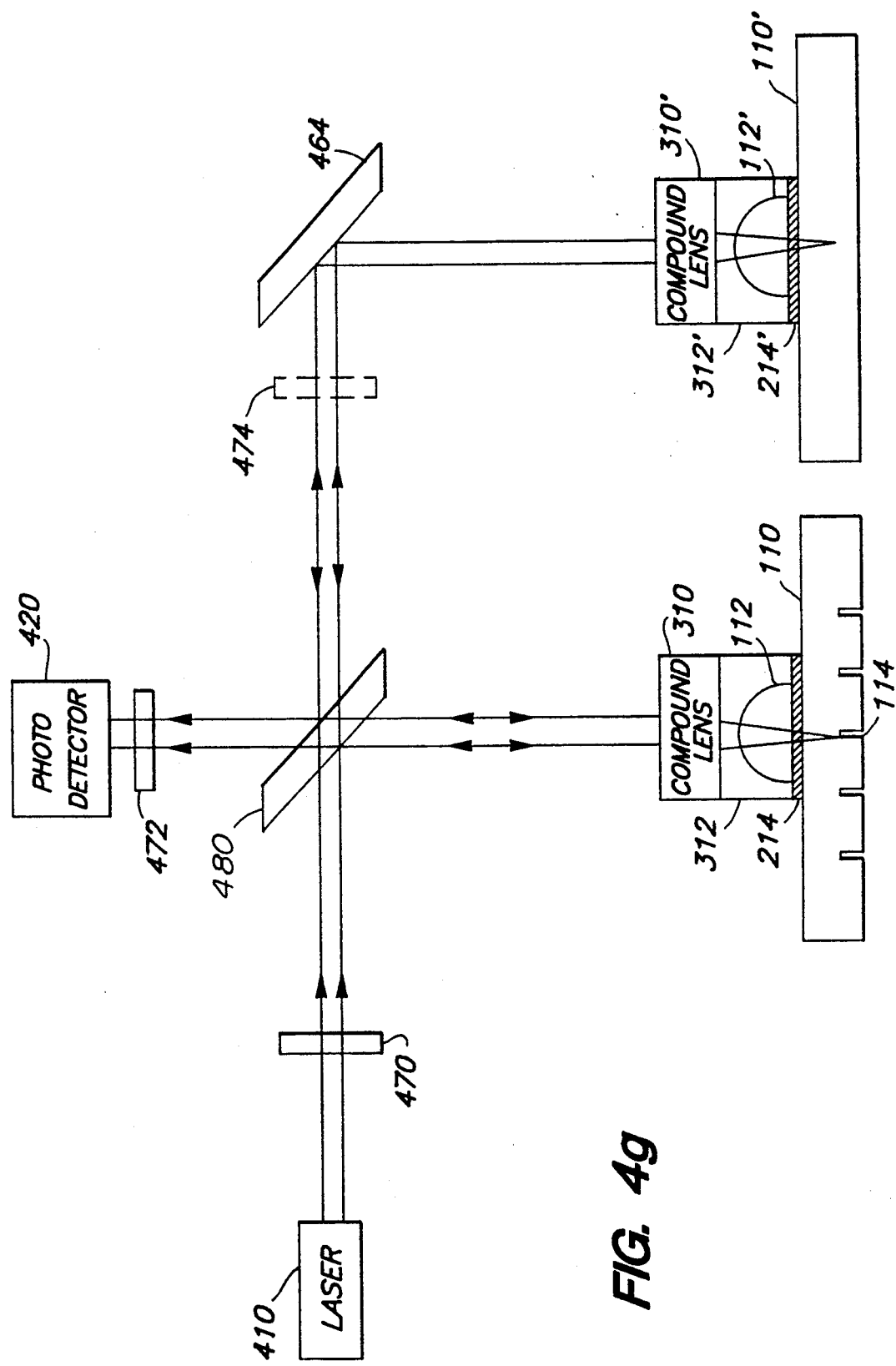

FIG. 4f is an elevation view of the imaging microscope described above in reference to FIG. 3 which has been modified to perform polarization measurements. The only differences between FIG. 4f and FIG. 2 are the addition of a polarizer 470 between the lens 318 and the beam splitter 320 and of an analyzer 472 between the beam splitter 320 and the photodetector array 314.

Since transmission of light through even a 50 nm gap depends somewhat on its polarization, it is not possible to achieve perfect rejection of the background illumination over the full field of view. Thus, the image detected by the photodetector array 314 includes undesirable artifacts. These artifacts, however, arise from a plane (e.g. the lens-wafer interface) which is far out of focus. Accordingly, they should vary relatively slowly over the field and be relatively insensitive to a small additional defocus. Defocus corresponds to a different phase shift for each plane wave component, but no substantial change in their relative strengths. Thus, the polarized signal resulting from the lens-wafer interface should not change very rapidly with defocus.

Stress, however, tends to be concentrated is relatively small regions of the wafer. Consequently, if an first image is taken at a focal plane including some stress-induced birefringence and a second image is taken which is defocussed somewhat from the first image, the background signal may be largely canceled out by subtracting the second image from the first image.

Voltage dependent effects may be measured using an AC voltage and separated from the largely DC background signal by conventional filtering techniques. Consequently, observation of the electro-optic effect in III-V compounds is not hindered by any polarization shift which may occur at the lens-wafer boundary.

FIG. 4g is an elevation view of a homodyne Linnik interferometer configured to make polarization measurements. In this configuration, the light from laser 410 is passed through a polarizer 470 to a beam splitter 480. The beam splitter 480 divides the light into two substantially equal components, directing one to the variable focus lens 312 coupled to the sample wafer 110 and directing the other to a mirror 464 which, in turn, directs it to the variable focus lens 312' coupled to the reference wafer 110'. Half of the reflected light from the sample wafer 110 passes through the beam splitter 480, through the analyzer 472 and onto the photodetector 420. Half of the light reflected from the sample wafer is deflected by the beam splitter 480, through the analyzer 472 and onto the photodetector 420 at substantially the same spot.

Alternatively, the analyzer 472 may be eliminated and replaced by an analyzer 474 positioned between the beam splitter 480 and the mirror 464. This analyzer would act only on the reference beam. When, however, the analyzed reference beam is combined with the reflected sample beam, the common polarization components can be canceled, for example, by chopping the beams at different frequencies, so that the resulting signals at the sum and difference frequencies are measures of the polarization effects caused by the sample wafer alone plus any differences between the polarization at the respective lens-wafer interfaces.

Figure 4H:
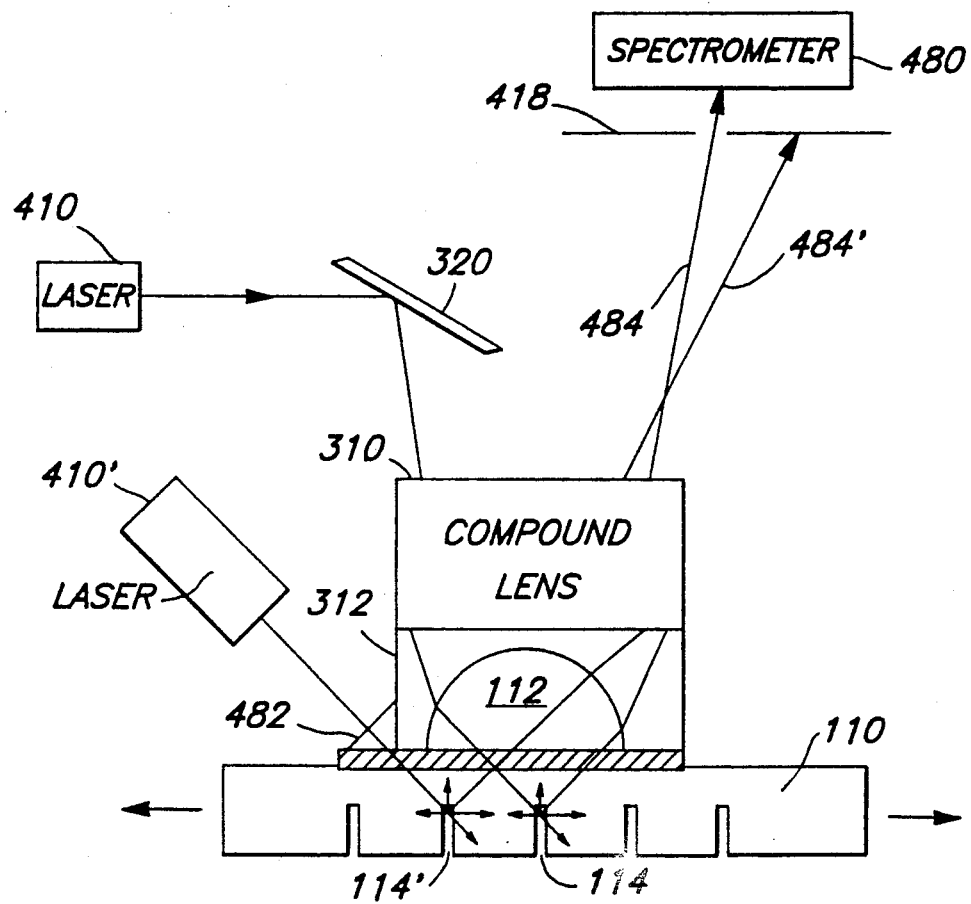
Figure 4I:
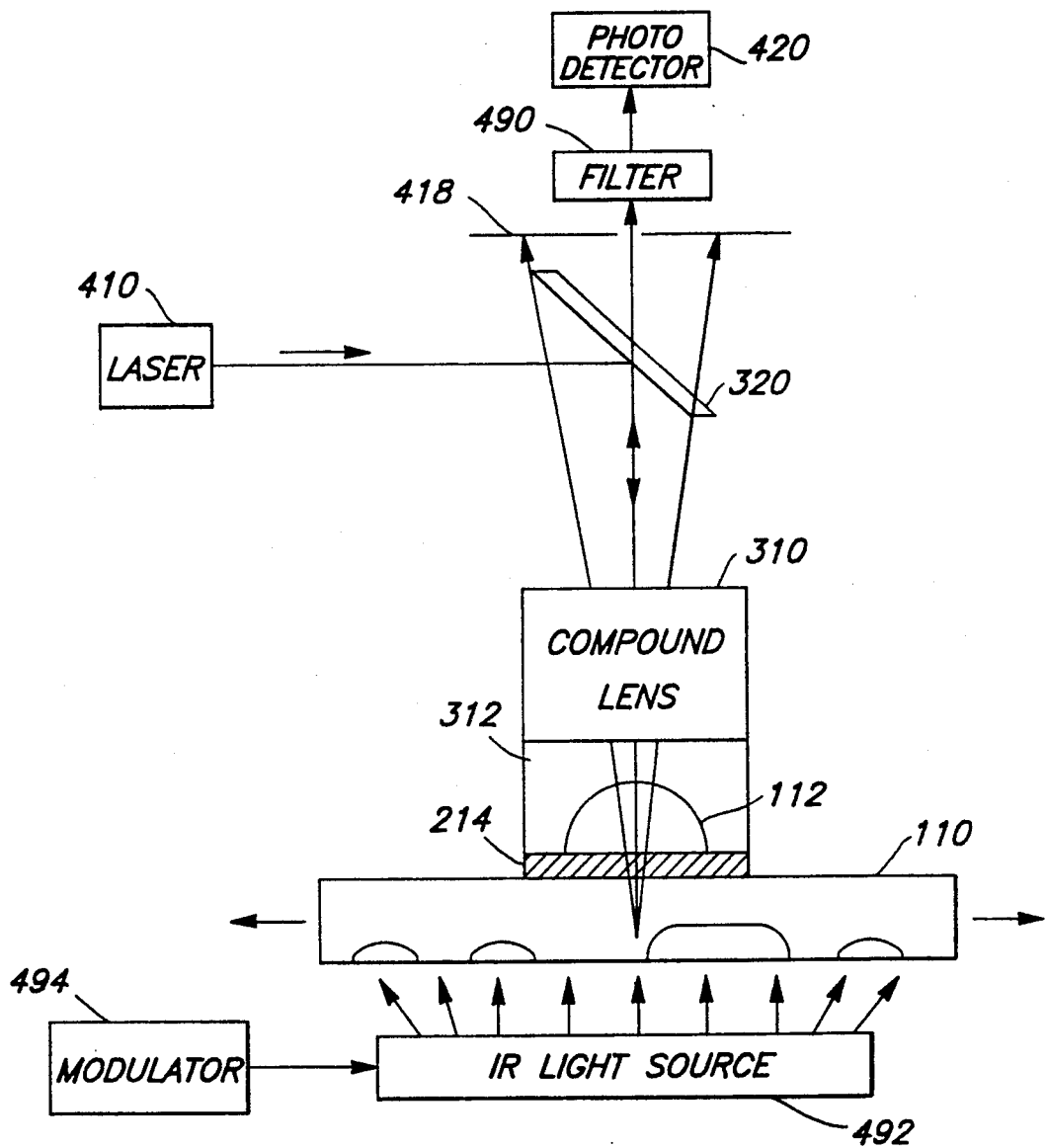

The high-NA lens system is also useful for making spectroscopic measurements. Two systems for performing these measurements are described below. FIG. 4h shows exemplary apparatus for performing Raman spectroscopy and FIG. 4i shows exemplary apparatus for performing absorption spectroscopy.

Raman spectroscopy may be used to detect stress in materials, contaminating materials in the bulk silicon or on the front surface or to detect residual process fluids in trenches. Raman spectroscopy is a linear effect, but since it involves a wavelength shift, it may also be done in a three-dimensional spatially resolved mode.

FIG. 4h is an elevation view of exemplary apparatus suitable for use in performing Raman spectroscopy. A laser 410 is configured to illuminate the wafer 110 at an angle less than the critical angle so that it becomes a propagating beam in the silicon wafer. When the beam encounters, for example, residual process fluid in one of the trenches 114, a Raman spectrum of the fluid is generated. As is well known, this spectrum is best viewed at an angle of 90° with respect to the illuminating beam. Consequently, the variable focus lens 312, a pinhole 418 and a spectrometer 480 are arranged with respect to the illuminator so that only that component of the scattered light which is at 90° with respect to the specularly reflected laser beam is passed to the spectrometer.

Two possible configurations for the Raman spectrometer are shown in FIG. 4h. In the first exemplary configuration, the illumination is provided by a laser 410 and a mirror 320. The beam passes through the variable focus lens 312 and into the wafer 110. The beam is specularly reflected by the fluid in the interior of the trench. A ray which is at an angle of 90° with respect to the specularly reflected light is passed back through the variable focus lens 312 to become the propagating beam 484. This beam is passed through the pinhole 418 onto the spectrometer 480.

In the second exemplary embodiment, a beam from the laser 410' is coupled into the wafer via a prism 482. This beam is specularly reflected by the fluid in the trench 114' to produce the propagating beam 484'. The spectrometer 480 and pinhole 418 are desirably moved to the right from their illustrated position to detect the beam 484'.

The high-NA lens 112 allows the light generated by illuminating the trench to propagate through the back surface of the wafer 110. Without the lens the component of the light containing the Raman lines may be totally internally reflected by the wafer.

FIG. 4i is an elevation view of an exemplary absorption spectrometer which incorporates the high-NA lens 112. In the apparatus shown in FIG. 4i, an infrared light having a frequency $f_0$ source 492 is amplitude modulated with a sinusoidal wave having a frequency $f_m$. The light from the source 492 is configured to uniformly illuminate the wafer 110 from the front side. A confocal microscope such as is shown in FIG. 4a is coupled to the back surface of the wafer 110. The frequency $f_1$ of the laser 410 is selected to be significantly different from $f_0$. Finally, a filter 490 is placed between the pinhole 418 and the photodetector 420. The filter 490 substantially removes light having frequencies close to $f_0$ while passing light having frequencies close to $f_1$.

In operation, when an area of doped silicon, 496 is illuminated both by the source 492 and by the laser 410, any nonlinear absorption effect will cause the light of the laser to be modulated with the signal $f_m$. By scanning the lens system 312 over the back surface of the wafer 110 (i.e. by moving the wafer across the page and out of the page beneath the lens system 312) and racking the focal point of the lens 312 from its minimum to its maximum, a three dimensional map, showing all nonlinear absorption effects, may be generated.

Figure 5A:
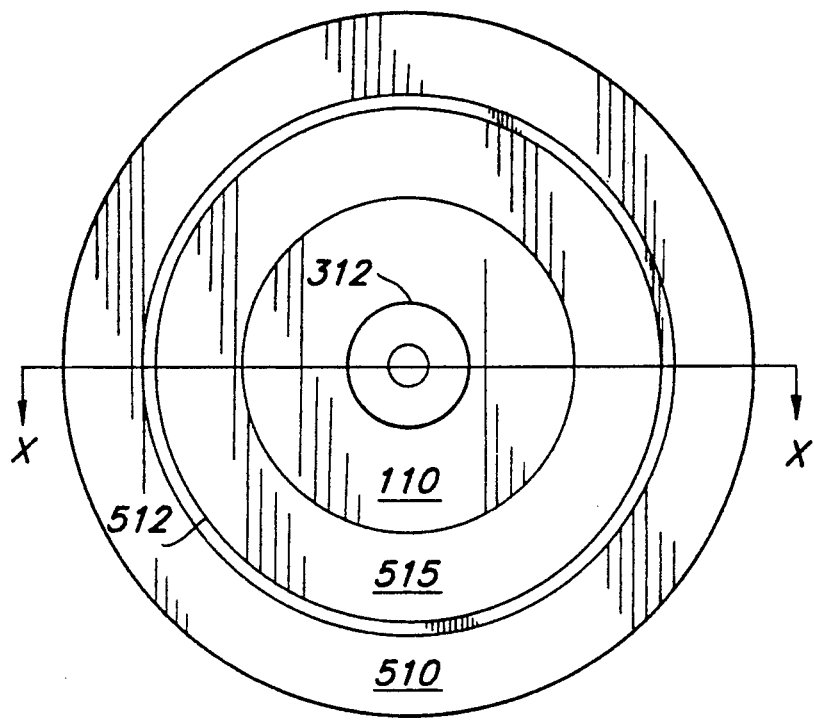
FIGS. 5a and 5b are respective top and cross sectional views of a semiconductor wafer and wafer chuck which illustrate an exemplary configuration for using the optical instruments shown in FIGS. 1a through 4i.
Figure 5B:
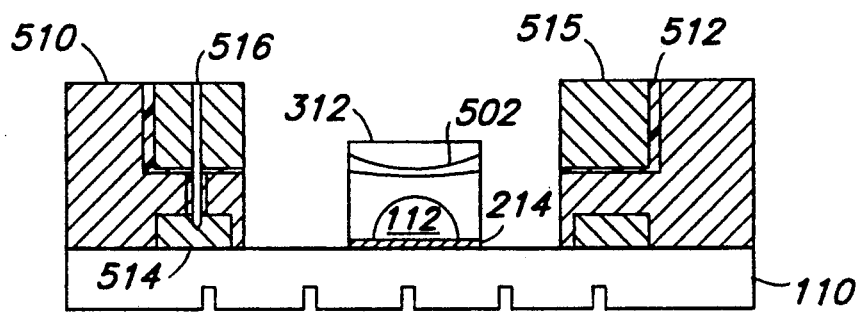

Up to this point, the description has focused on various optical instruments which may be fabricated using the high-NA lens 112. FIGS. 5a and 5b are a top-plan view and a side cross-sectional view, taken along the line x—x, which illustrates how the lens system 312 may be incorporated into a conventional wafer chuck, such as is commonly used to hold the wafer during various process steps.

The wafer chuck 510 differs from many existing chucks in that it is open in the center. The center opening provides an exposed area on the back surface of the wafer 110. When the wafer is mounted on the chuck, the wafer and the chuck may be moved relative to the lens assembly 312 to navigate any of the instruments described above. Alternatively, when the wafer must be held in a fixed position, for example, during a reactive ion etching step, a microscope is needed to determine the depth of trenches being etched, the lens assembly may be moved around beneath the wafer inside this opening.

Details on the implementation of an electrostatic wafer chuck may be found in a paper by G. Wardley entitled "Electrostatic Wafer Chuck for Electron Beam Microfabrication" Rev. Sci. Instrum., Vol. 44, No. 10, October 1973 pp 1506–1509, which is hereby incorporated by reference for its teaching on electrostatic wafer chucks.

Briefly, an electrostatic wafer chuck holds the wafer in place by applying electrostatic potentials of different polarities to different portions of the wafer. In this instance, one of the potentials is applied through the interface between the wafer 110 and the body 510 of the chuck. The other potential is applied via an insert 514 in the body of the chuck. The electrostatic potential is applied to the insert 514 by a connection 516 which extends through the body 510 at various points around the chuck body. The connection 516 joins the insert 514 to an electrode 515 on the back side of the chuck.

While the exemplary optical instruments have used optical coupling materials to couple the high-NA lens 112 to the back surface of the wafer 110, it is contemplated that any of the other methods (i.e. direct contact, soft index matching solid or air bearing) may be used to couple the lens to the wafer, as described above in reference to FIGS. 2a through 2d in place of the optical coupling material.

Although the lens 112 has been described as a hemispherical plano-convex lens, it is contemplated that other shaped lenses may be used. For example, a lens which is slightly less than a hemisphere may be particularly advantageous for certain of the instruments since it places the focal point of the lens 112 alone near the back surface of the wafer 110.

Although the invention has been described in terms of several exemplary embodiments, it is contemplated that it may be practiced with modifications within the spirit and scope of the appended claims.

The invention claimed is:

1. An interferometer useful in examining a sample semiconductor wafer having a front surface which includes features and a substantially featureless back surface and having an index of refraction greater than unity, said interferometer comprising:
   a reference semiconductor wafer having substantially featureless front and back surfaces;
   first and second plano-convex lenses having indices of refraction approximately equal to the index of refraction of the semiconductor wafers;
   means for optically coupling the first plano-convex lens to the back surface of the sample semiconductor wafer;
   means for optically coupling the second plano-convex lens to the back surface of the reference semiconductor wafer;
   illuminating means for generating light energy which is substantially coherent and monochromatic;
   beam splitting means configured to receive the light energy generated by said illuminating means for applying a first portion of the light energy to the sample wafer through the first plano-convex lens and for applying a second portion of the light energy to the reference wafer through the second plano-convex lens; and
   imaging means for combining light reflected from said sample semiconductor wafer with light reflected from said reference semiconductor wafer to generate an interference pattern representing features on the front of the sample semiconductor wafer.

2. The interferometer of claim 1 wherein:
   said beam splitting means includes an acousto-optic cell, responsive to a control signal for deflecting the first portion of the received light energy onto said sample wafer through the first plano-convex lens while passing the second portion undeflected to said reference wafer through the second plano-convex lens; and
   said interferometer further includes means, for generating said control signal at respectively different frequencies to condition the beam splitting means to deflect the first portion of the received light energy at respectively different positions onto said sample wafer through said first plano-convex lens.

3. A Raman spectrometer useful in examining a sample semiconductor wafer having a flat back surface and having an index of refraction greater than unity, said Raman spectrometer comprising:
   a plano-convex lens having an index of refraction approximately equal to the index of refraction of the semiconductor wafer;
   means for optically coupling the plano-convex lens to the back surface of the sample semiconductor wafer;
   illuminating means for generating light energy which is substantially coherent and monochromatic and for coupling the light energy into the semiconductor wafer at a predetermined angle of incidence and a predetermined position with respect to the plano-convex lens wherein reflected rays at approximately 90° to the specularly reflected wave in the semiconductor wafer are coupled through the optical coupling means and through the plano-convex lens;
   spatial filtering means for passing the rays reflected at 90° to the incident wave in the semiconductor wafer, provided by the plano-convex lens to the relative exclusion of other rays provided by the plano-convex lens; and
   spectrometer means for generating a Raman spectrogram from the rays passed by the spatial filtering means.

4. An absorption spectrometer useful in examining a sample semiconductor wafer having a flat back surface and having an index of refraction greater than unity, said absorption spectrometer comprising:
   a plano-convex lens having an index of refraction approximately equal to the index of refraction of the semiconductor wafer;
   means for optically coupling the plano-convex lens to the back surface of the sample semiconductor wafer;
   first illuminating means for generating light signals which are substantially monochromatic and for modulating said monochromatic light signals with a modulating signal having a frequency substantially less than the frequency of said monochromatic light signals and for illuminating said semiconductor wafer with said light signals;
   second illuminating means for generating a further light signal which is substantially monochromatic and coherent
   means for coupling said further light signal into said semiconductor wafer through said plano-convex lens;
   means for changing the focal point of the further light signal in the semiconductor wafer
   imaging means for detecting an image of the further light signal substantially at the focal point of the further light signal in the semiconductor wafer; and
   means for detecting absorption of the light signals provided by said first illuminating means by detecting modulation, by said modulating signal, of the further light signal in the image formed by said imaging means.

* * * * *